(12) United States Patent
Tanavade et al.

(10) Patent No.: US 10,709,908 B2
(45) Date of Patent: *Jul. 14, 2020

(54) SULFATE-FREE FORMULATIONS FOR SKIN CLEANSING

(71) Applicant: RHODIA OPERATIONS, Paris (FR)

(72) Inventors: Juie Tanavade, Franklin Park, NJ (US); Rajesh Patel, Pennington, NJ (US); James Griffin, Jackson, NJ (US)

(73) Assignee: RHODIA OPERATIONS, Aubervilliers (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/097,450

(22) Filed: Apr. 13, 2016

(65) Prior Publication Data

US 2016/0296446 A1    Oct. 13, 2016

Related U.S. Application Data

(60) Provisional application No. 62/146,498, filed on Apr. 13, 2015.

(51) Int. Cl.
| | | |
|---|---|---|
| *A61K 8/49* | (2006.01) | |
| *A61K 8/46* | (2006.01) | |
| *A61Q 19/00* | (2006.01) | |
| *A61Q 19/10* | (2006.01) | |
| *A61K 8/81* | (2006.01) | |
| *A61K 8/42* | (2006.01) | |
| *A61K 8/36* | (2006.01) | |
| *A61K 8/44* | (2006.01) | |

(52) U.S. Cl.
CPC .............. *A61Q 19/10* (2013.01); *A61K 8/361* (2013.01); *A61K 8/442* (2013.01); *A61K 8/466* (2013.01); *A61K 2800/28* (2013.01); *A61K 2800/30* (2013.01)

(58) Field of Classification Search
CPC ........ A61Q 19/10; A61K 8/442; A61K 8/466; A61K 8/361; A61K 2800/28; A61K 2800/30
See application file for complete search history.

(56) References Cited

U.S. PATENT DOCUMENTS

| 8,114,824 B1 | 2/2012 | Dasgupta et al. |
| 8,470,753 B2* | 6/2013 | D'Aversa ............... A61K 8/345 |
| | | 510/123 |
| 8,865,147 B2 | 10/2014 | Rizk et al. |
| 2011/0245125 A1* | 10/2011 | Tsaur ..................... A61K 8/361 |
| | | 510/127 |
| 2011/0275552 A1 | 11/2011 | Patel et al. |
| 2015/0044157 A1 | 2/2015 | Kulkarni et al. |
| 2015/0093348 A1 | 4/2015 | Sato et al. |
| 2016/0095804 A1 | 4/2016 | Xavier et al. |

FOREIGN PATENT DOCUMENTS

| EP | 1076554 B1 | 10/2004 |
| KR | 100439461 B1 | 7/2004 |
| WO | 2015110356 A1 | 11/2005 |
| WO | 2018005745 A1 | 1/2018 |

OTHER PUBLICATIONS

"Topical Drug Treatment in Acne", Gollnick, H. et al.; Dermatology 1998; 196:119-125.
"Shampoo", GNPD, Mintel, Aug. 1, 2014, XP002757962.
"StraightAway Shampoo", GNPD, Mintel, Jun. 1, 2014, XP002784087, CAG Beauty.
"3-in-Wash", GNPD, Mintel, Mar. 1, 2014, Kale Naturals, XP002784088.
"Advances in Formulating High Performance, Sulfate-Free Cleansing Products", Dr. Tony Gough, Apr. 2, 2014, pp. 1-45, XP055174853, Innospec IS Presentation.
"Miracare TM Soft 313", Nov. 1, 2015, pp. 1-4, XP055501266.

* cited by examiner

*Primary Examiner* — Sarah Pihonak
*Assistant Examiner* — Jason Deck

(57) ABSTRACT

The present disclosure provides a cleansing composition that includes from about 20% to about 40% by weight of a primary anionic surfactant; from about 10% to about 30% by weight of an amphoacetate; from about 10% to about 30% by weight of a sultaine; and from about 0.5% to about 2% by weight of a fatty acid, wherein the amounts are based upon the total weight of the composition and the composition is free of anionic alkyl sulfates and alkyl ether sulfates.

13 Claims, 2 Drawing Sheets

SULFATE-FREE FORMULATIONS FOR SKIN CLEANSING

CROSS-REFERENCE TO RELATED APPLICATION

The present application claims the benefit of priority under 35 U.S.C. § 119(e) of U.S. Provisional Application Ser. No. 62/146,498, filed on Apr. 13, 2015, the entire disclosure of which is incorporated herein by reference.

BACKGROUND

At the present time, most of the commercially available personal care compositions are based on sulfate-containing surfactants such as sodium lauryl sulfate, (SLS), ammonium lauryl sulfate (ALS), sodium laureth sulfate (SLES) or ammonium laureth sulfate (ALES). SLS, ALS, SLES and ALES are the most widespread sulfate-containing surfactants used in this field as they are inexpensive and as they exhibit at the same time satisfactory cleansing and foaming properties.

However personal care compositions including sulfate-containing surfactants present also significant drawbacks. As a matter of fact sulfate-containing surfactants such as SLS are known to be liable to give rise to tolerance problems, especially on the skin and the eyes. Another drawback of sulfate-containing surfactants is their tendency to strip the skin, scalp or hair of its natural oils, fats or proteins contained at their surface. In the long term the repeated use of personal care compositions including sulfate-containing surfactants may therefore cause irritation to the skin or scalp and/or give damage on hair fibers.

In recent times there is thus an increasing demand for personal care compositions including safe, environment friendly, and/or milder surfactants, and especially for personal care compositions free of sulfate-containing surfactants.

One of the major challenges of formulating sulfate-free personal care compositions lies in the need to maintain mildness, satisfactory cleansing, conditioning and foaming properties without negatively impacting viscosity of the overall composition.

SUMMARY

It is thus an object of the present disclosure to address the ever increasing demand in the market for personal care compositions that are free of sulfate-containing surfactants without negatively affecting viscosity and foaming properties.

The present disclosure provides a cleansing composition that includes from about 20% to about 40% by weight of a primary anionic surfactant; from about 10% to about 30% by weight of an amphoacetate; from about 10% to about 30% by weight of a sultaine; and from about 0.5% to about 2% by weight of a fatty acid, wherein the amounts are based upon the total weight of the composition and the composition is free of anionic alkyl sulfates and alkyl ether sulfates.

Also described is a skin cleansing method that includes the steps of applying a cleansing composition according to the present disclosure to an area of skin on a body; washing the area of skin on the body; and rinsing the area of skin on the body.

DETAILED DESCRIPTION

Figure 1:
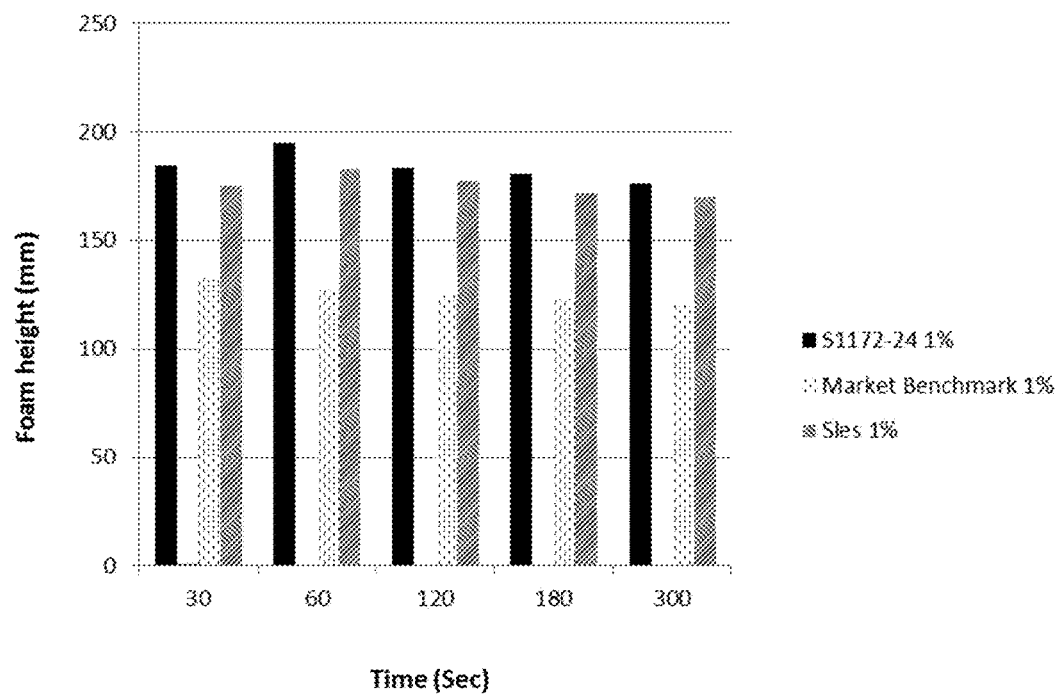
FIG. 1 depicts foam analysis of batch S1172-24 against 1% SLES and 1% Market Benchmark moisturizing body wash.

One of the aims of the present disclosure is to provide personal care compositions that exhibit good foaming properties and maintain a satisfactory viscosity, while at the same time being free of sulfate-containing surfactants.

In general, cleansing compositions according to the present disclosure include from about 20% to about 40% by weight of a primary anionic surfactant; from about 10% to about 30% by weight of an amphoacetate; from about 10% to about 30% by weight of a sultaine; and from about 0.5% to about 2% by weight of a fatty acid, wherein the amounts are based upon the total weight of the composition and the composition is free of anionic alkyl sulfates and alkyl ether sulfates. Thus, the following anionic surfactants are preferably not present in the composition of the present disclosure: salts of alkyl sulfates, of alkylamide sulfates, of alkyl ether sulfates, of alkylamido ether sulfates, of alkylaryl ether sulfates, of monoglyceride sulfates.

While specific embodiments are discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the phrase "foaming properties" refers to flash foam and foam volume, which are among the main factors affecting the consumer perception about the foam quality. Well-known tests, notably as described in the experimental part, may be used to measure these factors.

In certain embodiments, the pH of the composition ranges from 7.5 to 10.4

In certain embodiments, the primary anionic surfactant is selected from sodium cocoyl glycinate, sodium methyl cocoyl taurate, and sodium lauryl glycinate.

In other embodiments, the amphoacetate is sodium lauroamphoacetate.

In other embodiments, the sultaine is cocamidopropyl hydroxysultaine.

In certain embodiments, the fatty acid is lauric acid.

In other embodiments, the composition further includes water.

Compositions according to the present disclosure are suitable for various cleansing applications. In certain embodiments, the composition is a concentrated body wash formulation. In other embodiments, the concentrated body wash formulation has a pH of 8.00.

In certain embodiments, the composition includes at least one structuring agent. In one aspect, the structuring agent is a hydrophobically-modified alkali-swellable emulsion polymer. In another aspect, the structuring agent is present in an amount from about 5% to about 10% by weight and the amount is based upon the total weight of the composition.

In certain aspects, adding a structuring agent allows for incorporating oils into the composition which will provide moisturizing benefits. In certain embodiments, the oil is selected from oils of mineral origin, oils of vegetable origin, and mixtures or associations thereof. In some embodiments, the oil is present in the form of dispersed particles or droplets.

In certain embodiments, oils of mineral origin are selected from (INCI names): Petrolatum, Mineral Oil, Hydrogenated Polydodecene, Hydrogenated Polydecene, Polydecene, and combinations thereof.

In certain embodiments, oils of vegetable origin are selected from (INCI names): *Adansonia Digitata* Seed Oil; *Alpinia Speciosa* Leaf Oil; *Argemone Mexicana* Oil; *Brassica Oleracea* Italica (Broccoli) Seed Oil; *Calodendrum Capense* Nut Oil; *Calophyllum Inophyllum* Seed Oil; *Camellia Chekiangoleosa* Seed Oil; *Carica Papaya* Seed Oil; *Cedrus Deodara* Seed Oil; *Cocos Nucifera* (Coconut) Oil; *Crambe Abyssinica* Seed Oil; Egg Oil; *Fragaria Ananassa* (Strawberry) Seed Oil; Hydrogenated *Camellia Oleifera* Seed Oil; Hydrogenated Evening Primrose Oil; Hydrogenated Hazelnut Oil; Hydrogenated Lanolin; Hydrogenated Macadamia Seed Oil; Hydrogenated Rice Bran Oil; Hydrogenated Sesame Seed Oil; Hydroxylated Jojoba Oil; Isobutylated Lanolin Oil Lanolin Oil; *Lesquerella Fendleri* Seed Oil; Marmot Oil; Mink Oil; *Ocimum Tenuiflorum* Oil; *Orbignya Cohune* Seed Oil; Ostrich Oil; *Phormium Tenax* Seed Oil; PPG-40-PEG-60 Lanolin Oil; PPG-12-PEG-65 Lanolin Oil; *Pongamia Glabra* Seed Oil; *Pinus Parviflora* Seed Oil; *Sclerocarya Birrea* Seed Oil; *Schleichera Trijuga* Seed Oil; *Simmondsia Chinensis* (Jojoba) Seed Oil; *Sorbus Aucuparia* Seed Oil; *Zea Mays* (Corn) Oil; *Bertholletia Excelsa* Seed Oil PEG-8 Esters; Coconut Oil Methylpropanediol Esters; Jojoba Oil PEG-8 Esters; Hydrogenated Castor Oil Behenyl Esters; Hydrogenated Castor Oil Cetyl Esters; Hydrogenated Castor Oil Dimer Dilinoleate; Hydrogenated Castor Oil Stearyl Esters; Hydrogenated Olive Oil Caprylyl Esters; Hydrogenated Olive Oil Cetyl Esters; Hydrogenated Olive Oil Decyl Esters; Hydrogenated Olive Oil Hexyl Esters; Hydrogenated Olive Oil Lauryl Esters; Hydrogenated Olive Oil Myristyl Esters; Hydrogenated Olive Oil Stearyl Esters; *Orbignya Oleifera* Seed Oil PEG-8 Esters; *Passiflora Edulis/Passiflora Incarnata* Seed Oils PEG-8 Esters; *Brassica Campestris* (Rapeseed) Oil Unsaponifiables; *Brassica Oleracea Botrytis* (Cauliflower) Oil Unsaponifiables; *Butyrospermum Parkii* (Shea Butter) Unsaponifiables; Canola Oil Unsaponifiables; *Citrus Aurantifolia* (Lime) Seed Oil Unsaponifiables; *Citrus Aurantium Dulcis* (Sweet Orange) Seed Oil Unsaponifiables; *Citrus Grandis* (Grapefruit) Seed Oil Unsaponifiables; Hydrogenated Apricot Oil Unsaponifiables; Hydrogenated Grapefruit Seed Oil Unsaponifiables; Hydrogenated Lime Seed Oil Unsaponifiables; Hydrogenated Olive Oil Unsaponifiables; Hydrogenated Orange Seed Oil Unsaponifiables; Hydrogenated Sweet Almond Oil Unsaponifiables; Hydrogenated Wheat Germ Oil Unsaponifiables; *Helianthus Annuus* (Sunflower) Seed Oil Unsaponifiables; *Lupinus Albus* Oil Unsaponifiables; *Medicago Sativa* (Alfalfa) Oil Unsaponifiables; *Olea Europaea* (Olive) Oil Unsaponifiables; 30 *Olea Europaea* (Olive) Fruit Unsaponifiables; *Persea Gratissima* (Avocado) Oil Unsaponifiables; *Prunus Armeniaca* (Apricot) Kernel Oil Unsaponifiables; *Sesamum Indicum* (Sesame) Oil Unsaponifiables; *Triticum Vulgare* (Wheat) Germ Oil Unsaponifiables; and *Zea Mays* (Corn) Oil Unsaponifiables.

In certain embodiments, the composition includes one or more additives selected from vitamins, botanical extracts, moisturizers, emollients, preservatives, exfoliating agents, and fragrances.

In certain aspects, the one or more additives are selected from arachis oil, castor oil, cocoa butter, coconut oil, corn oil, cotton seed oil, olive oil, palm kernel oil, rapeseed oil, safflower seed oil, sesame seed oil and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropy stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A,C,D,E,K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as alnus, arnica, artemisia capillaris, asiasarum root, calendula, chamomile. Cnidium, comfrey, fennel, galla rhois, hawthorn, houttuynia, hypericum, jujube, kiwi, licorice, magnolia, olive, peppermint, philodendron, salvia, sasa albomarginata, imidazoles such as ketoconazole and elubiol, those anti-acne agents described in Gollnick, H. et al. 196(1) Dermatology Sebaceous Glands, Acne and Related Disorders, 119-157 (1998), which is incorporated by reference herein to the extent that it is not inconsistent with the present application; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacaleitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; and reflectants, such as mica, alumina, calcium silicate, glycol dioleate, glycol distearate, silica, sodium magnesium fluorosilicate.

In certain aspects, the composition is incorporated into body cleansers, facial cleansers, or hand soap formulations. In other embodiments, the composition is incorporated into a foam wash by diluting the composition to 8-10% solids.

In certain embodiments, the composition of the present disclosure is prepared using a concentrated flowable surfactant composition. Certain embodiments include concentrates that are suitable to prepare compositions of the present disclosure. Concentrates including a mixture of surfactants are advantageous as their use would reduce the need to transport a plurality of individual components.

Personal care compositions are usually prepared by mixing individual surfactants and any additional ingredients. These components may be supplied as concentrated solutions which are diluted and/or and combined in appropriate ratios by the formulator. The present disclosure covers any surfactant concentrate to be used as component ingredient to prepare a composition of the present disclosure, and especially to surfactant concentrates containing limited levels of water (more advantageous from a cost and environmental perspective).

Also described herein is a skin cleansing method that includes applying a cleansing composition according to the present disclosure to an area of skin on a body; washing the area of skin on the body; and rinsing the area of skin on the body.

The present disclosure will further be described by reference to the following examples. The following examples are merely illustrative and are not intended to be limiting. Unless otherwise indicated, all percentages are by weight of the total composition.

EXAMPLE 1

Preparation of Compositions.

Water and anionic surfactant (sodium cocoyl glycinate or sodium methyl cocoyl taurate) were mixed together. The mixture was heated to 65° C. At 65° C., fatty acid (lauric acid) was added and mixed until it completely melted and a uniform solution was formed. At this point, the heat was turned off to cool the batch. The amphoteric surfactants (sodium lauroamphoacetate and cocamidopropyl hydroxysultaine) were added, and the mixture was cooled to room temperature (25° C.). The pH was checked and recorded. Adjustments were made to a pH of 9.5-10.4 using a 50% sodium hydroxide solution. A clear formulation was obtained at the end of the reaction process.

TABLE 1

Composition details. (Amounts shown are percent active).

| Batch # | Geropon ® CG-3S (Sodium cocoyl glycinate) | Miranol ® Ultra L-32 (sodium lauroamphoacetate) | Mackam ® CBS-50G (Cocamidopropyl hydroxysulatine) | Gerapon ® TC-42 LQ(sodium cocoyl methyl Taurate) | Stability |
|---|---|---|---|---|---|
| S1172-24 | 8 | 8 | 10 | 0.00 | Stable |
| S1172-43 | 0.00 | 8 | 10 | 8 | Stable |

EXAMPLE 2

Further Studies

Further studies were carried out on composition S1172-24. Some results are provided in Table 2.

TABLE 2

Effect of pH on the viscosity and stability of the S1172-24 blend.

| pH | Viscosity* | Color Gardner | Stability |
|---|---|---|---|
| 7.5 | 8,150 | 1.00 | Precipitates at FT and 45 |
| 8.5 | 1200 | 0.5 | stable |
| 9.5 | 320 | 0.5 | stable |
| 10.5 | 380 | 0.5 | Stable |

*All viscosity measurements were done using a Brookfield viscometer LV #3 @ 3 rpm.

The Stability study was done over a period of 3 months and 3 freeze thaw cycles. An increase in the viscosity was observed at all temperatures during the duration of the stability study. As seen in Table 2, the concentrate was unstable at a pH of 7.5 and hence the investigation at this pH range was stopped. A pH of 8.5-10.00 was optimal for the development of this blend.

EXAMPLE 3

Spec Evaluation of the Composition

Table 3 shows the spec evaluation of the concentrate S1172-24. All readings were carried out at pH 9.5.

TABLE 3

| Spec development. | |
|---|---|
| Appearance | Clear, flowable liquid |
| pH as is | 9.5 |
| Viscosity 25 C. LV#3 @ 6 rpm | 560 cps |
| Color G @25 C. | 0.7 |
| % Solids (microwave method) | 33.94 |
| pH, 5% solution | 9.92 |
| Salts, % | 5.29 |

EXAMPLE 4

Stability Study

A full stability study was run on batch S1172-24 for a period of 3 months. Samples were aged at 25° C., 45° C. and freeze thaw and tested for pH, viscosity and color shift at intervals of 2, 4, 8 and 12 weeks. There was a steady increase in viscosity over the aging period which is likely attributed to the Miranol® Ultra L-32. No major color change was observed during the aging cycle.

TABLE 4

| Specification table with lower and upper limits. | | |
|---|---|---|
| Spec | min | max |
| Appearance | Clear pourable liquid | |
| pH | 9.5 | 10.4 |
| Viscosity (LV#3 @ 6 rpm) | Max 5000 cps | |
| Color Gardner | 2 max | |
| % solids (Microwave) | 33.5 | 35.5 |
| % NaCl | 4.5 | 6.5 |

These limits were challenged by overcharge experiments where the surfactant was overcharged by 10% each at a time. The specs were tested and it was found that while there was an increase in the viscosity and % solids it was still within the specification. Multi lot variations carried on the concentrated provided similar results.

EXAMPLE 5

Foam Height Analysis

The foam test was performed with a Kruss DFA100 Dynamic Foam Analyzer. The experiment was carried in accordance with SOP CRTB-SOP-0147. 200 mL 1% solutions of the benchmark and prototype was prepared. 50mL test solution was accurately weighed into the test cylinder. Gas flow was set to 0.3 L/min and gas was pumped for 25 seconds. The foam height was set for 6 minutes.

Foam height analysis was done on a 1%, 0.75% and 0.5% solution of batch S1172-24 against 1% SLES solution at pH 10 and a market benchmark moisturizing body wash. FIG. 1 shows the foam height comparison of 1% S1172-24 with 1% SLES solution (Rhodapex® ES-2/K). The initial foam height of the concentrate was higher than that of the SLES solution. Further, even after 300 seconds the foam height did not decrease significantly indicating stable foam.

EXAMPLE 6

Zein Analysis

The zein test is a method for analyzing the dermal irritation potential of a surfactant or a product. The zein assay was performed in accordance with SOP CRTB-SOP-0146.

Figure 2:
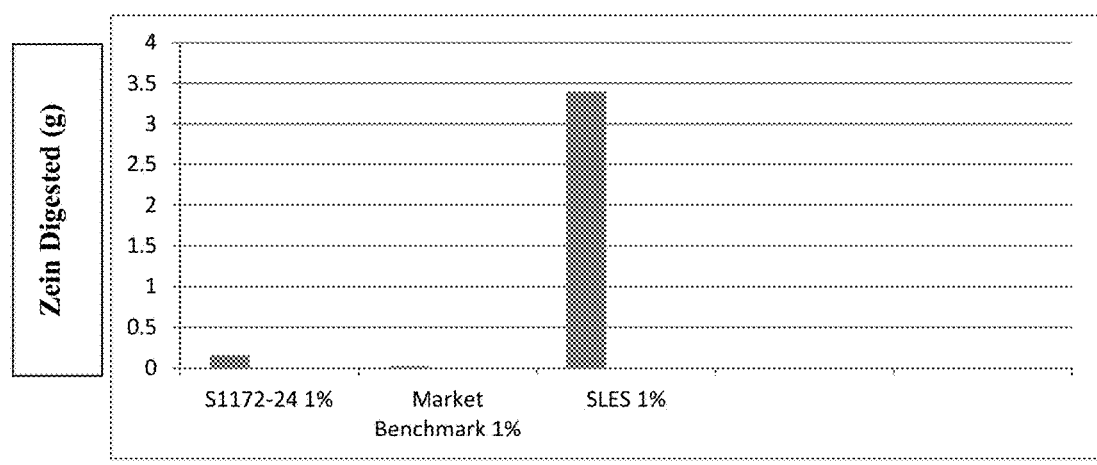
FIG. 2 depicts zein analysis comparing S1172-24 against 1% SLES and 1% Market Benchmark.

0.4 gm of zein protein was added to 1% test solutions and mixed for 60 minutes. The solution was then filtered with filter paper. The solids collected on the filter paper were dried overnight in a 45° C. oven. The final weight of the zein was taken and percent zein dissolved was calculated using the below formula:

Total zein (g) added to the solution−Undissolved (g) zein after drying 0.5 [total grams of surfactant] =Gram zein dissolved/Gram surfactant Zein analysis was done on 1%, 0.75% and 0.5% solutions of S1172-24 against 1% SLES solution and 1% market benchmark moisturizing body wash. As seen in FIG. 2, the Zein numbers for S1172-24, even at 1%, are significantly lower than that of 1% SLES demonstrating that S1172-24 is milder than SLES.

EXAMPLE 7

Exfoliating Composition

Water was combined with Polyacrylate-33 and mixed for 20 minutes. S1172-24 was blended with the aqueous Polyacrylate-33 mixture until the blend was completely homogenized. The pH was adjusted to 7.0-7.5 with 50% caustic solution. Mica and apricot scrubbing beads were added to the blend and mixed until uniformly distributed in the batch. Finally, fragrance and preservative were mixed into the batch (S1172-140). S1172-140 exhibited a pH ranging from 7.0 to 7.5 and viscosity ranging from 7,000 to 15,000 cps (Brookfield viscometer LV #3).

TABLE 5

| Composition details. (Amounts shown are percent active). | |
|---|---|
| Water | 61.75 |
| S1172-24 (Sodium cocoyl glycinate, sodium Lauroamphoacetate, cocamidopropyl hydroxysultaine) | 28.57 |
| Rheomer ®-33T (Polyacrylate-33) | 8.33 |
| phenoxyethanol | 0.5 |
| Fragrance | 0.5 |
| Mica | 0.1 |
| Apricot scrubbing seeds | 0.2 |

Figure 3:
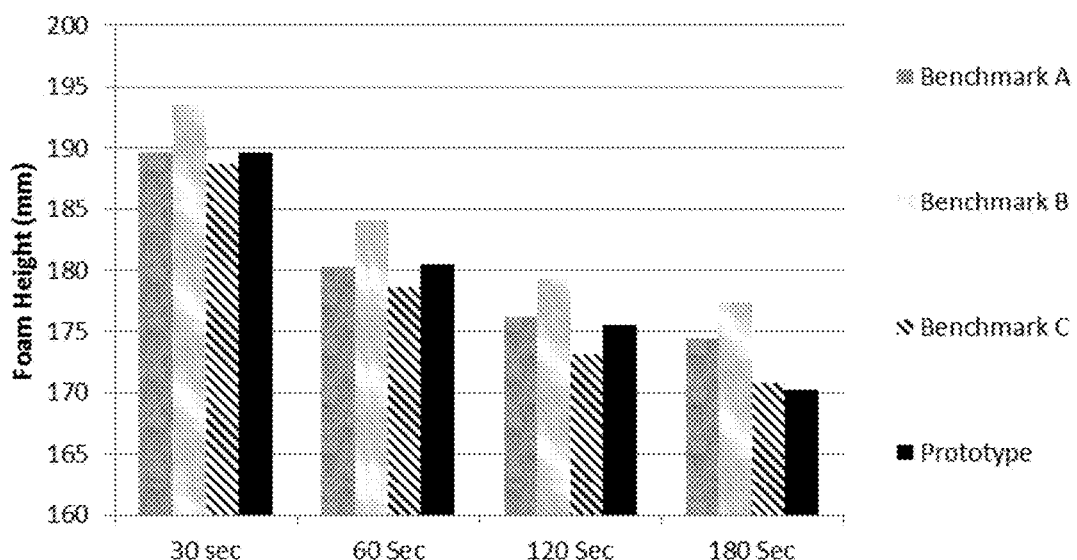
FIG. 3 depicts foam analysis of batch S1172-140 ("Prototype") against three Market Benchmark exfoliating body washes.

Foam height analysis was performed on S1172-140 ("Prototype") against three market benchmark exfoliating body washes. FIG. 3 shows the foam height comparison. Foam height of S1172-140 is at parity with market benchmarks compared.

EXAMPLE 8

Moisturizing Composition

Water was combined with Polyacrylate-33 and mixed well in a main beaker. Acetamide MEA and lacatamide MEA (Mackamide® LAME-100) and Polyglycerol-3 were added to the mixture. The resulting mixture was then heated to 65° C. S1172-24 was added to the mixture in the main beaker and mixed until completely uniform. In a separate beaker, the petrolatum was heated to 65° C. When both phases were at 65° C., the petrolatum was added to the main beaker and mixed well until completely homogenous. The resulting batch was then cooled to room temperature and the pH was adjusted to 7.0. At 40° C., titanium dioxide, fragrance and preservative were added. The resulting composition exhibited a "white lotion" appearance with a viscosity ranging from 10,000 to 15,000 cps (Brookfield viscometer LV #3).

TABLE 6

Composition details. (Amounts shown are percent active).

| | |
|---|---|
| Water | QS |
| Rheomer ® 33T (Polyacrylate-33) | 8.33 |
| Polyglycerol-3 | 1.5 |
| Mackamide ® LAME-100 (Acetamide MEA and Lacatamide MEA) | 1.5 |
| S1172-24 (Sodium Cocoyl Glycinate, Sodium Lauroamphoacetate, Cocamidopropyl Hydroxysultaine) | 25.14 |
| Petrolatum | 3 |
| Titanium Dioxide | 0.25 |
| Fragrance | 0.5 |
| Preservative | 0.2 |

Figure 4:
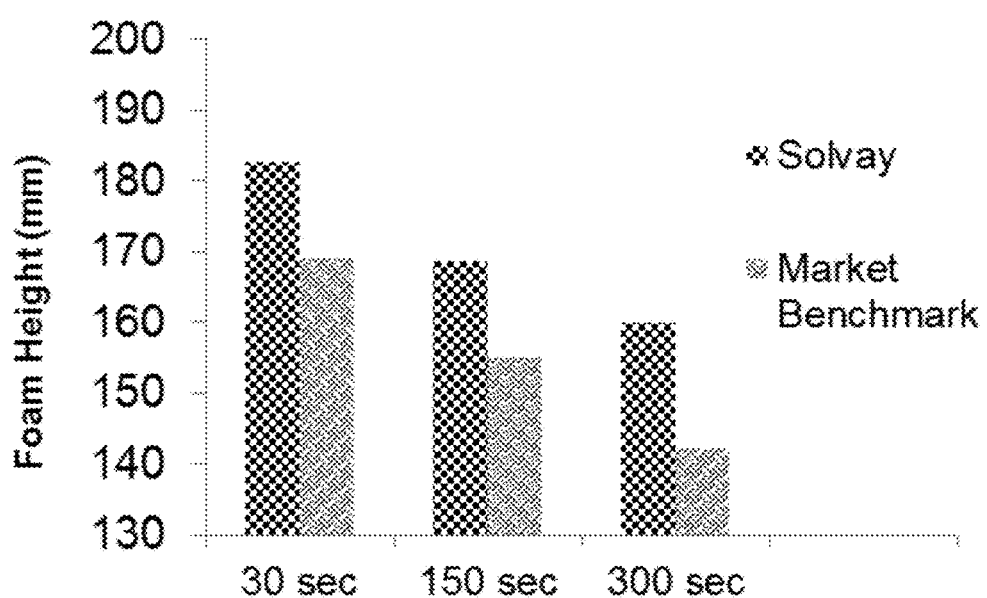
FIG. 4 depicts foam analysis of a moisturizing composition of the present disclosure ("Solvay") against a Market Benchmark moisturizing composition.

Foam height analysis was performed on the moisturizing composition of the present disclosure ("Solvay") against a market benchmark moisturizing composition. FIG. 4 shows the foam height comparison. Foam height of the moisturizing composition is better than that of the market benchmark.

The disclosed subject matter has been described with reference to specific details of particular embodiments thereof. It is not intended that such details be regarded as limitations upon the scope of the disclosed subject matter except insofar as and to the extent that they are included in the accompanying claims.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components, substances and steps. As used herein the term "consisting essentially of" shall be construed to mean including the listed components, substances or steps and such additional components, substances or steps which do not materially affect the basic and novel properties of the composition or method. In some embodiments, a composition in accordance with embodiments of the present disclosure that "consists essentially of" the recited components or substances does not include any additional components or substances that alter the basic and novel properties of the composition. If there is any conflict in the usages of a word or term in this specification and one or more patent or other documents that may be incorporated herein by reference, the definitions that are consistent with this specification should be adopted.

We claim:

1. A liquid cleansing composition consisting of:
   a. from about 20% to about 40% by weight of an anionic surfactant selected from the group consisting of sodium cocoyl glycinate, sodium methyl cocoyl taurate, and sodium lauryl glycinate;
   b. from about 10% to about 30% by weight of an amphoacetate; and
   c. from about 10% to about 30% by weight of a sultaine;
   d. from about 0.5% to about 2% by weight of a fatty acid;
   e. optionally one or more members selected from the group consisting of water, structuring agents, vitamins, botanical extracts, moisturizers, emollients, preservatives, exfoliating agents, oils, and fragrances,
   wherein the amounts are based upon the total weight of the composition and the composition is free of anionic alkyl sulfates and alkyl ether sulfates.

2. The composition of claim 1, wherein the pH ranges from 7.5 to 10.4.

3. The composition of claim 1, wherein the anionic surfactant is sodium cocoyl glycinate.

4. The composition of claim 1, wherein the anionic surfactant is sodium methyl cocoyl taurate.

5. The composition of claim 1, wherein the anionic surfactant is sodium lauryl glycinate.

6. The composition of claim 1, wherein the amphoacetate is sodium lauroamphoacetate.

7. The composition of claim 1, wherein the sultaine is cocamidopropyl hydroxysultaine.

8. The composition of claim 1, wherein the fatty acid is lauric acid.

9. The composition of claim 1, wherein the composition includes water.

10. The composition of claim 1, wherein the composition includes at least one structuring agent.

11. The composition of claim 10, wherein the structuring agent is present in an amount from about 5% to about 10% by weight and the amount is based upon the total weight of the composition.

12. The composition of claim 10, wherein the structuring agent is a hydrophobically-modified alkali-swellable emulsion polymer.

13. A skin cleansing method comprising applying the cleansing composition of claim 1 to an area of skin on a body; washing the area of skin on the body; and rinsing the area of skin on the body.

* * * * *